United States Patent
Larsen et al.

(10) Patent No.: US 11,912,696 B2
(45) Date of Patent: Feb. 27, 2024

(54) COMPOUNDS AND METHODS FOR DETECTION OF NITRIC OXIDE

(71) Applicant: Promega Corporation, Madison, WI (US)

(72) Inventors: Matthew A. Larsen, Madison, WI (US); Hui Wang, Madison, WI (US); Wenhui Zhou, Madison, WI (US); Peter Hofsteen, Madison, WI (US); Jolanta Vidugiriene, Madison, WI (US)

(73) Assignee: Promega Corporation, Madison, WI (US)

( * ) Notice: Subject to any disclaimer, the term of this patent is extended or adjusted under 35 U.S.C. 154(b) by 0 days.

(21) Appl. No.: 17/937,210

(22) Filed: Sep. 30, 2022

(65) Prior Publication Data

US 2023/0117418 A1  Apr. 20, 2023

Related U.S. Application Data

(60) Provisional application No. 63/251,395, filed on Oct. 1, 2021.

(51) Int. Cl.
*C07D 417/04* (2006.01)
*C07D 277/64* (2006.01)

(52) U.S. Cl.
CPC .......... *C07D 417/04* (2013.01); *C07D 277/64* (2013.01)

(58) Field of Classification Search
CPC .................................................... C07D 417/04
See application file for complete search history.

(56) References Cited

FOREIGN PATENT DOCUMENTS

| CN | 1072663802 B | 8/2020 |
|---|---|---|
| WO | WO 2006/130551 | 12/2006 |
| WO | WO 2011/112996 | 9/2011 |
| WO | WO 2014/127360 A1 | 8/2014 |

OTHER PUBLICATIONS

Registry/Zregistry (CAS Registrysm) Sep. 2016 2 pages.*
Bartlett "Exploiting Chemical Diversity for Drug Discovery" Edited by Paul A Bartlett and Michael Entzeroth, The Royal Society of Chemistry, 2006, pp. 113-118.*
Kim "PubChem in 2021: new data content and improved web interfaces" Nucleic Acids Research, 2021, vol. 49, Database issue Published online Nov. 5, 2020.*
Irwin "ZINC—A Free Database of Commercially Available Compounds for Virtual Screening" J. Chem. Inf. Model. 2005, 45, 177-182.*
"Find ETDs Home » Thesis Resources » Find ETDs" Online: "https://ndltd.org/thesis-resources/find-etds/" Accessed Jan. 31, 2023.*
Islam "A Smart Molecule for Selective Sensing of Nitric Oxide: Conversion of NO to HSNO; Relevance of Biological HSNO Formation." Inorganic Chemistry, 2017, 56(8), 4324-4331.*
Han et al. "Turn-On Fluorescence Probe for Nitric Oxide Detection and Bioimaging in Live Cells and Zebrafish" ACS Sens. 2019, 4, 309-316.
International Search Report and Written Opinion dated Dec. 23, 2022, Intl. Appl. No. PCT/EP2022/077390, 12 pages.
Ju et al., "A caged 2-hydroxyethyl luciferin for bioluminescence imaging of nitroxyl in living cells" Luminescence 2020, 35:1384-1390.
Kim et al., "Naphthalimide-4-(4-nitrophenyl)thiosemicarbazide: A Fluorescent Probe for Simultaneous Monitoring of Viscosity and Nitric Oxide in Living Cells" Anal. Chem. 2021, 93:4391-4397.
Kojima et al. "Detection and Imaging of Nitric Oxide with Novel Fluorescent Indicators: Diaminofluoresceins" Anal. Chem. 1998, 70, 2446-2453.
Ren et al., "A Biocompatible Condensation Reaction for the Labeling of Terminal Cysteine Residues on Proteins" Angew. Chem. Int. Ed. 2009, 48:9658-9662.
Takura et al., "New Class of Bioluminogenic Probe Based on Bioluminescent Enzyme-Induced Electron Transfer: BioLeT" J. Am. Chem. Soc. 2015, 137(12): 4010-4013.
Yang et al. "A Highly Selective Low-Background Fluorescent Imaging Agent for Nitric Oxide" J. Am. Chem. Soc. 2010, 132, 13114-13116.
Ye et al. "Simultaneous nitric oxide and dehydroascorbic acid imaging by combining diaminofluoresceins and diaminorhodamines" J. Neurosci. Methods 168 (2008) 373-382.
Zielonka et al., "On the use of peroxy-caged luciferin (PCL-1) probe for bioluminescent detection of inflammatory oxidants in vitro and in vivo—Identification of reaction intermediates and oxidant-specific minor products" Free Radical Biology and Medicine 2016, 32-42.

* cited by examiner

*Primary Examiner* — David K O'Dell
(74) *Attorney, Agent, or Firm* — Casimir Jones, S.C.; Anne M. Reynolds

(57) ABSTRACT

Disclosed herein are compounds that can be used to selectively detect nitric oxide in samples. Also disclosed herein are compositions comprising the compounds and methods of detecting nitric oxide using the compounds.

20 Claims, 4 Drawing Sheets

COMPOUNDS AND METHODS FOR DETECTION OF NITRIC OXIDE

CROSS-REFERENCE TO RELATED APPLICATIONS

This application claims priority to and the benefit of U.S. Provisional Patent Application No. 63/251,395, filed on Oct. 1, 2021, which is incorporated herein by reference in its entirety.

TECHNICAL FIELD

Disclosed herein are compounds that can be used to selectively detect nitric oxide in samples. Also disclosed herein are compositions comprising the compounds and methods of detecting nitric oxide using the compounds.

BACKGROUND

Nitric oxide (NO) is a reactive molecule with a half-life of ~2-6 seconds and is formed from L-arginine by nitric oxide synthases (eNOS, iNOS, and nNOS). NO is an important signaling molecule that regulates vasoconstriction and immune responses. NO also plays a critical role in oxidative stress as it rapidly reacts with superoxide to form cytotoxic peroxynitrite. Thus, methods for directly detecting cellular nitric oxide are highly sought after. Current methods for detection of NO include indirect colorimetric measurement through detection of its terminal products (nitrite and nitrate) via the Griess reaction and various NO-reactive fluorophores. However, some commonly used probes, such as those including o-phenylene diamine based reactive moieties, tend to react with bis electrophiles, such as dehydroascorbic acid, to generate false positives. There is accordingly a need for quantitative and specific assays to detect NO.

SUMMARY

In one aspect, the disclosure provides a compound of formula (I):

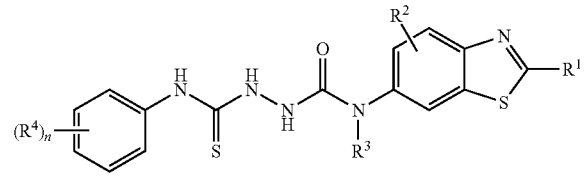

(I)

or a salt thereof, wherein:
$R^1$ is selected from —CN and

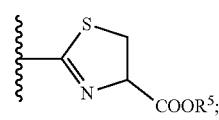

$R^2$ is selected from hydrogen and halo;
$R^3$ is selected from hydrogen, $C_1$-$C_6$ alkyl, and hydroxy-$C_1$-$C_6$-alkyl;
n is 0, 1, 2, or 3;
each $R^4$ is independently selected from $C_1$-$C_6$ alkyl, $C_2$-$C_6$ alkenyl, $C_2$-$C_6$ alkynyl, $C_1$-$C_6$ heteroalkyl, $C_1$-$C_6$ alkoxy, $C_1$-$C_6$ haloalkyl, $C_1$-$C_6$ haloalkoxy, halo, hydroxy, amino, cyano, nitro, —COOR$^a$, and —CONR$^b$R$^c$;
$R^5$ is selected from hydrogen and $C_1$-$C_4$ alkyl; and
$R^a$, $R^b$, and $R^c$ are each independently selected from hydrogen, $C_1$-$C_6$ alkyl, $C_2$-$C_6$ alkenyl, $C_2$-$C_6$ alkynyl, and $C_1$-$C_6$ heteroalkyl.

In some embodiments, $R^1$ is —CN. In some embodiments, $R^1$ is

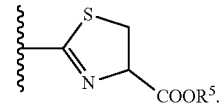

In some embodiments, $R^5$ is selected from hydrogen and methyl.
In some embodiments, $R^2$ is hydrogen.
In some embodiments, $R^3$ is hydrogen. In some embodiments, $R^3$ is hydroxy-$C_2$-$C_4$-alkyl. In some embodiments, $R^3$ is —CH$_2$CH$_2$CH$_2$OH.
In some embodiments, n is 0. In some embodiments, n is 1. In some embodiments, $R^4$ is selected from methoxy and nitro.
In some embodiments, the compound is selected from:

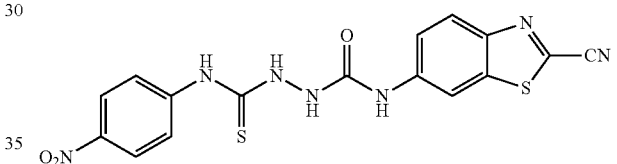

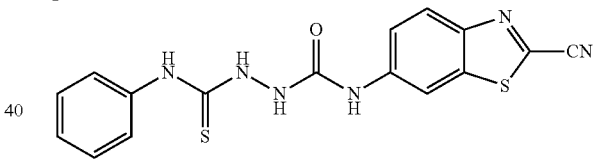

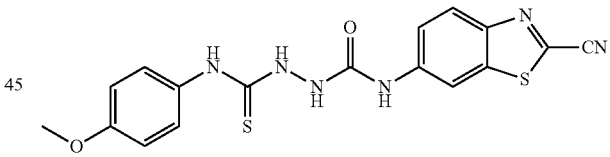

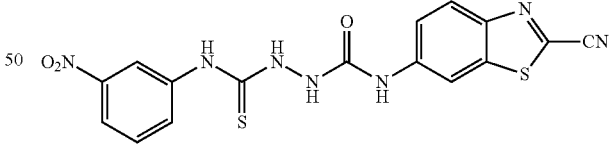

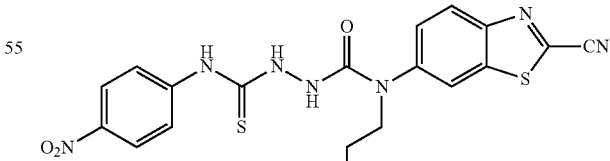

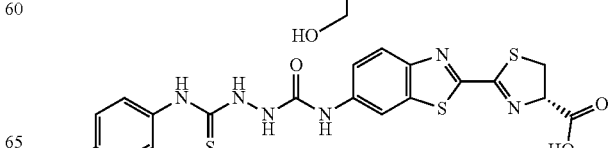

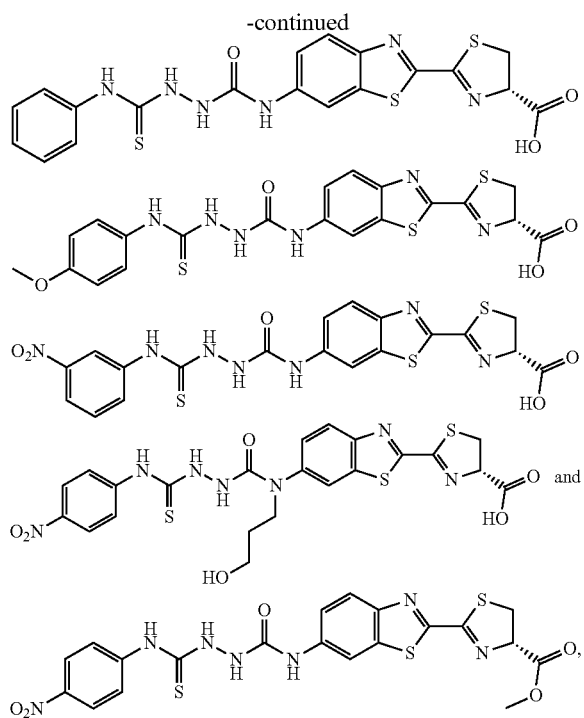

and salts thereof.

In another aspect, disclosed herein is a method of detecting nitric oxide in a sample, comprising:
- contacting the sample with a compound disclosed herein (e.g., a compound of formula (I)), or a salt thereof;
- contacting the sample with a luciferin-utilizing luciferase, if it is not already present in the sample; and
- detecting luminescence in the sample.

In some embodiments, the sample comprises live cells. In some embodiments, the cells express the luciferin-utilizing luciferase. In some embodiments, the method comprises adding the luciferin-utilizing luciferase to the sample. In some embodiments, the luciferin-utilizing luciferase is a firefly luciferase or a click beetle luciferase.

In another aspect, disclosed herein is a kit comprising a compound disclosed herein (e.g., a compound of formula (I)), or a salt thereof. In some embodiments, the kit further comprises a luciferin-utilizing luciferase enzyme or a nucleotide sequence encoding a luciferin-utilizing luciferase enzyme. In some embodiments, the kit further comprises a buffer reagent.

Other aspects and embodiments will become apparent in light of the following description and drawings.

DETAILED DESCRIPTION

Figure 1:
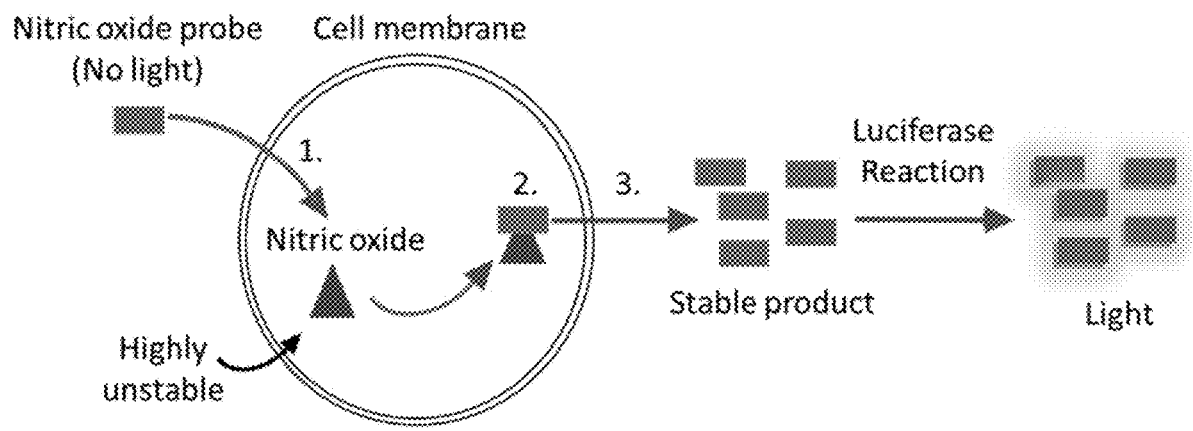
FIG. 1 shows a schematic overview of a method of detecting nitric oxide in a cell using compounds such as those disclosed herein.
Figure 2:
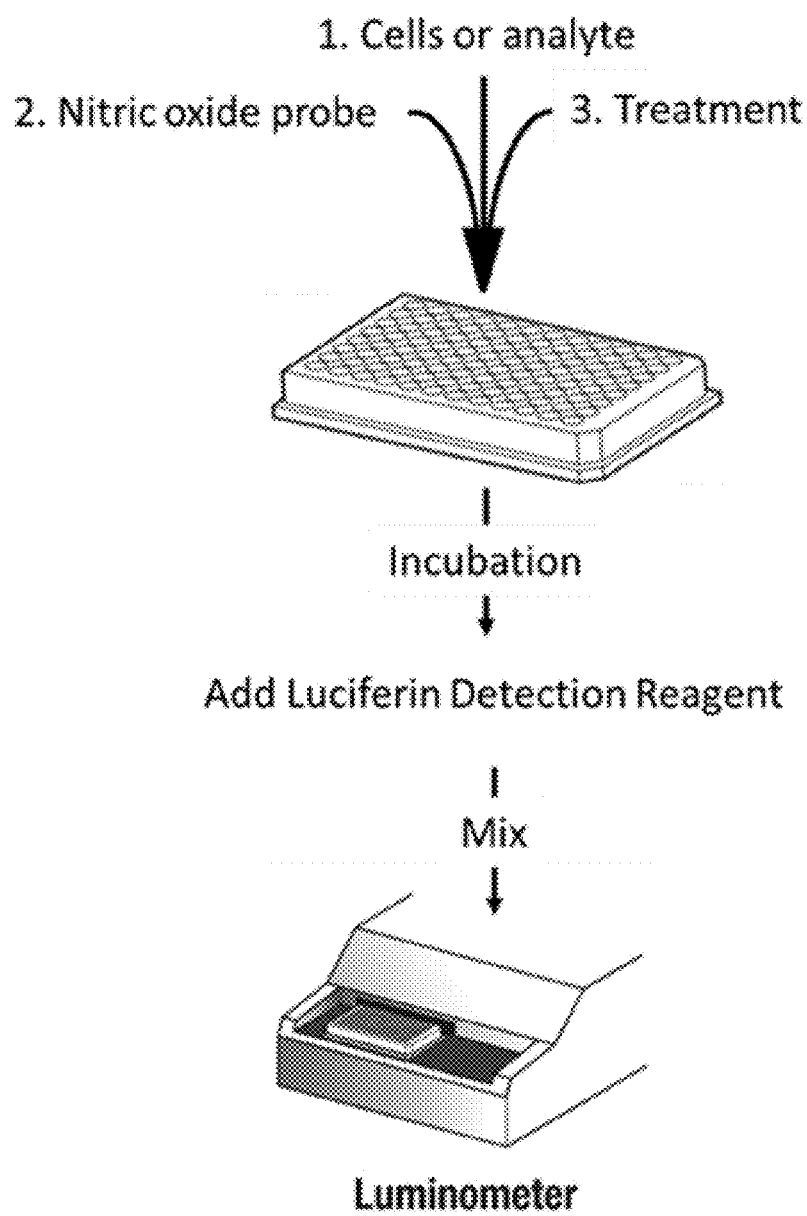
FIG. 2 shows a schematic overview of a luminescence assay to detect nitric oxide in a sample of cells or other analyte; the "treatment" step refers to addition of an unknown experimental component (e.g., a drug candidate), which can be added before, after, or simultaneously with the nitric oxide probe.

Disclosed herein are probe compounds, particularly caged aminoluciferin and aminocyanobenzothiazole compounds and derivatives thereof, that have high specificity for detection of nitric oxide over other reactive nitrogen and oxygen species. Upon reaction with nitric oxide, a stable reporter product is formed, allowing assays to be conducted in a homogeneous "add and read" plate-based format or in kinetic mode by media sampling.

Definitions

Although any methods and materials similar or equivalent to those described herein can be used in the practice or testing of embodiments described herein, some preferred methods, compositions, devices, and materials are described herein. However, before the present materials and methods are described, it is to be understood that this invention is not limited to the particular molecules, compositions, methodologies, or protocols as herein described as these may vary in accordance with routine experimentation and optimization. It is also to be understood that the terminology used in the description is for the purpose of describing the particular versions or embodiments only and is not intended to limit the scope of the embodiments described herein.

Unless otherwise defined herein, scientific and technical terms used in connection with the present disclosure shall have the meanings that are commonly understood by those of ordinary skill in the art. For example, any nomenclatures used in connection with, and techniques of, cell and tissue culture, molecular biology, immunology, microbiology, genetics and protein and nucleic acid chemistry and hybridization described herein are those that are well known and commonly used in the art. The meaning and scope of the terms should be clear; in the event, however of any latent ambiguity, definitions provided herein take precedent over any dictionary or extrinsic definition. Further, unless otherwise required by context, singular terms shall include pluralities and plural terms shall include the singular.

As used herein and in the appended claims, the singular forms "a", "an", and "the" include plural reference unless the context clearly dictates otherwise. Thus, for example, reference to "a peptide" is a reference to one or more peptides and equivalents thereof known to those skilled in the art, and so forth.

As used herein, the term "and/or" includes any and all combinations of listed items, including any of the listed items individually. For example, "A, B, and/or C" encompasses A, B, C, AB, AC, BC, and ABC, each of which is to be considered separately described by the statement "A, B, and/or C."

As used herein, the term "comprise" and linguistic variations thereof denote the presence of recited feature(s), element(s), method step(s), etc., without the exclusion of the presence of additional feature(s), element(s), method step(s), etc. Conversely, the term "consisting of" and linguistic variations thereof, denotes the presence of recited feature(s), element(s), method step(s), etc., and excludes any unrecited feature(s), element(s), method step(s), etc., except for ordinarily-associated impurities. The phrase "consisting essentially of" denotes the recited feature(s), element(s), method step(s), etc., and any additional feature(s), element(s), method step(s), etc., that do not materially affect the basic nature of the composition, system, or method. Many embodiments herein are described using open "comprising" language. Such embodiments encompass multiple closed "consisting of" and/or "consisting essentially of" embodiments, which may alternatively be claimed or described using such language.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

"Luminescence" refers to the light output of a luciferase enzyme under appropriate conditions, e.g., in the presence of a suitable substrate such as a luciferin (e.g., aminoluciferin) or aminocyanobenzothiazole compound (e.g., one that has been generated following reaction of nitric oxide with a compound of formula (I)). The light output may be measured as an instantaneous or near-instantaneous measure of light output (which is sometimes referred to as "T=0" luminescence or "flash") at the start of the luminescence reaction, which may be initiated upon addition of the luciferin substrate. The reaction chamber (e.g., a plate such as a 96-well plate) may be situated in a reading device which can measure the light output, e.g., using a luminometer or photomultiplier. The light output or luminescence may also be measured over time, for example in the same reaction chamber for a period of seconds, minutes, hours, etc. The light output or luminescence may be reported as the average over time, the half-life of decay of signal, the sum of the signal over a period of time, or the peak output. Luminescence may be measured in Relative Light Units (RLUs).

As used herein, the term "sample" is used in its broadest sense. In one sense, it is meant to include a specimen or culture obtained from any source as well as biological and environmental samples. Biological samples may be obtained from animals (including humans) and encompass fluids, solids, tissues, and gases. Biological samples include blood products such as plasma, serum, and the like. Sample may also refer to cells, cell lysates or purified forms of the enzymes, peptides, and/or polypeptides described herein (e.g., a purified protein sample). Cell lysates may include cells that have been lysed with a lysing agent or lysates such as rabbit reticulocyte or wheat germ lysates. Sample may also include in vitro samples and cell-free samples, such as cell-free expression systems. Environmental samples include environmental material such as surface matter, soil, water, crystals, and industrial samples. Sample may also include purified samples, such as purified protein samples. Such examples are not however to be construed as limiting the sample types applicable to the present invention.

Definitions of specific functional groups and chemical terms are described in more detail below. For purposes of this disclosure, the chemical elements are identified in accordance with the Periodic Table of the Elements, CAS version, Handbook of Chemistry and Physics, 75$^{th}$ Ed., inside cover, and specific functional groups are generally defined as described therein. Additionally, general principles of organic chemistry, as well as specific functional moieties and reactivity, are described in Sorrell, Organic Chemistry, 2$^{nd}$ edition, University Science Books, Sausalito, 2006; Smith, March's Advanced Organic Chemistry: Reactions, Mechanism, and Structure, 7$^{th}$ Edition, John Wiley & Sons, Inc., New York, 2013; Larock, Comprehensive Organic Transformations, 3$^{rd}$ Edition, John Wiley & Sons, Inc., New York, 2018; and Carruthers, Some Modern Methods of Organic Synthesis, 3$^{rd}$ Edition, Cambridge University Press, Cambridge, 1987; the entire contents of each of which are incorporated herein by reference.

As used herein, the term "alkyl" refers to a straight or branched saturated hydrocarbon chain. The alkyl chain can include, e.g., from 1 to 30 carbon atoms ($C_1$-$C_{30}$ alkyl), 1 to 24 carbon atoms ($C_1$-$C_{24}$ alkyl), for example 1 to 16 carbon atoms ($C_1$-$C_{16}$ alkyl), 1 to 14 carbon atoms ($C_1$-$C_{14}$ alkyl), 1 to 12 carbon atoms ($C_1$-$C_{12}$ alkyl), 1 to 10 carbon atoms ($C_1$-$C_{10}$ alkyl), 1 to 8 carbon atoms ($C_1$-$C_8$ alkyl), 1 to 6 carbon atoms ($C_1$-$C_6$ alkyl), or 1 to 4 carbon atoms ($C_1$-$C_4$ alkyl). Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, n-decyl, n-undecyl, and n-dodecyl.

As used herein, the term "alkenyl" refers to a straight or branched hydrocarbon chain containing at least one carbon-carbon double bond. The double bond(s) may be located at any position within the hydrocarbon chain. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, and 3-decenyl.

As used herein, the term "alkynyl" refers to a straight or branched hydrocarbon chain containing at least one carbon-carbon triple bond. The triple bond(s) may be located at any position within the hydrocarbon chain. Representative examples of alkynyl include, but are not limited to, ethynyl, propynyl, and butynyl.

As used herein, the term "alkoxy" refers to an alkyl group, as defined herein, appended to the parent molecular moiety through an oxygen atom. Representative examples of alkoxy include, but are not limited to, methoxy, ethoxy, propoxy, 2-propoxy, butoxy, and tert-butoxy.

As used herein, the term "amino" refers to a group —$NR_xR_y$, wherein $R_x$ and $R_y$ are selected from hydrogen and alkyl (e.g., $C_1$-$C_4$ alkyl).

As used herein, the term "aryl" refers to an aromatic carbocyclic ring system having a single ring (monocyclic) or multiple rings (bicyclic or tricyclic) including fused ring systems, and zero heteroatoms. As used herein, aryl contains 6-20 carbon atoms ($C_6$-$C_{20}$ aryl), 6 to 14 ring carbon atoms ($C_6$-$C_{14}$ aryl), 6 to 12 ring carbon atoms ($C_6$-$C_{12}$ aryl), or 6 to 10 ring carbon atoms ($C_6$-$C_{10}$ aryl). Representative examples of aryl groups include, but are not limited to, phenyl, naphthyl, anthracenyl, and phenanthrenyl.

As used herein, the term "cycloalkyl" refers to a saturated carbocyclic ring system containing three to ten carbon atoms and zero heteroatoms. The cycloalkyl may be monocyclic, bicyclic, bridged, fused, or spirocyclic. Representative examples of cycloalkyl include, but are not limited to, cyclopropyl, cyclobutyl, cyclopentyl, cyclohexyl, cycloheptyl, cyclooctyl, cyclononyl, cyclodecyl, adamantyl, bicyclo[2.2.1]heptanyl, bicyclo[3.2.1]octanyl, and bicyclo[5.2.0]nonanyl.

As used herein, the term "halogen" or "halo" means F, Cl, Br, or I.

As used herein, the term "haloalkyl" refers to an alkyl group, as defined herein, in which at least one hydrogen atom (e.g., one, two, three, four, five, six, seven or eight hydrogen atoms) is replaced with a halogen. In some embodiments, each hydrogen atom of the alkyl group is replaced with a halogen. Representative examples of haloalkyl include, but are not limited to, fluoromethyl, difluoromethyl, trifluoromethyl, 2,2,2-trifluoroethyl, and 3,3,3-trifluoropropyl.

As used herein, the term "haloalkoxy" means a haloalkyl group, as defined herein, that is appended to the parent molecular moiety through an oxygen atom. Representative examples of haloalkoxy include, but are not limited to, difluoromethoxy, trifluoromethoxy, and 2,2,2-trifluoroethoxy.

As used herein, the term "heteroalkyl" means an alkyl group, as defined herein, in which one or more of the carbon atoms (and any associated hydrogen atoms) are each independently replaced with a heteroatom group such as —NH—, —O—, —S—, —S(O)—, —S(O)$_2$—, and the like. By way of example, 1, 2, or 3 carbon atoms may be independently replaced with the same or different heteroatom group. Examples of heteroalkyl groups include, but are not limited to, —CH$_2$OCH$_3$, —CH$_2$SCH$_3$, —CH$_2$NHCH$_3$, —CH$_2$N(CH$_3$)$_2$, —CH$_2$S(O)CH$_3$, and —CH$_2$S(O)$_2$CH$_3$. Heteroalkyl also includes groups in which a carbon atom of the alkyl is oxidized (i.e., is —C(O)—).

As used herein, the term "hydroxy" means an —OH group.

As used herein, the term "hydroxyalkyl" means an alkyl group, as defined herein, in which at least one hydrogen atom has been replaced with a hydroxy group.

When a group or moiety can be substituted, the term "substituted" indicates that one or more (e.g., 1, 2, 3, 4, 5, or 6; in some embodiments 1, 2, or 3; and in other embodiments 1 or 2) hydrogens on the group indicated in the expression using "substituted" can be replaced with a selection of recited indicated groups or with a suitable substituent group known to those of skill in the art (e.g., one or more of the groups recited below), provided that the designated atom's normal valence is not exceeded. Substituent groups include, but are not limited to, alkyl, alkenyl, alkynyl, alkoxy, acyl, amino, amido, amidino, aryl, azido, carbamoyl, carboxyl, carboxyl ester, cyano, cycloalkyl, cycloalkenyl, guanidino, halo, haloalkyl, haloalkoxy, heteroalkyl, heteroaryl, heterocyclyl, hydroxy, hydrazino, imino, oxo, nitro, phosphate, phosphonate, sulfonic acid, thiol, thione, or combinations thereof.

As used herein, in chemical structures the indication:

represents a point of attachment of one moiety to another moiety (e.g., a substituent group to the rest of the compound).

For compounds described herein, groups and substituents thereof may be selected in accordance with permitted valence of the atoms and the substituents, such that the selections and substitutions result in a stable compound, e.g., which does not spontaneously undergo transformation such as by rearrangement, cyclization, elimination, etc.

Where substituent groups are specified by their conventional chemical formulae, written from left to right, they optionally encompass substituents resulting from writing the structure from right to left, e.g., —CH$_2$O— optionally also recites —OCH$_2$—, and —OC(O)NH— also optionally recites —NHC(O)O—.

Compounds

Disclosed herein are compounds of formula (I):

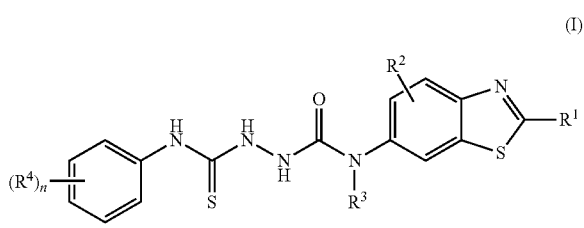

or a salt thereof, wherein:

R$^1$ is selected from —CN and

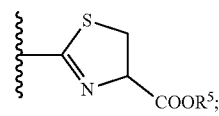

R$^2$ is selected from hydrogen and halo;

R$^3$ is selected from hydrogen, C$_1$-C$_6$ alkyl, and hydroxy-C$_1$-C$_6$-alkyl;

n is 0, 1, 2, or 3;

each R$^4$ is independently selected from C$_1$-C$_6$ alkyl, C$_2$-C$_6$ alkenyl, C$_2$-C$_6$ alkynyl, C$_1$-C$_6$ heteroalkyl, C$_1$-C$_6$ alkoxy, C$_1$-C$_6$ haloalkyl, C$_1$-C$_6$ haloalkoxy, halo, hydroxy, amino, cyano, nitro, —COOR$^a$, and —CONR$^b$R$^c$;

R$^5$ is selected from hydrogen and C$_1$-C$_4$ alkyl; and

R$^a$, R$^b$, and R$^c$ are each independently selected from hydrogen, C$_1$-C$_6$ alkyl, C$_2$-C$_6$ alkenyl, C$_2$-C$_6$ alkynyl, and C$_1$-C$_6$ heteroalkyl.

In some embodiments, R$^1$ is —CN. In some embodiments, R$^1$ is

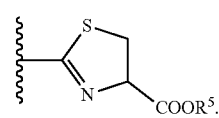

In some embodiments, R$^5$ is selected from hydrogen and methyl. In some embodiments, R$^5$ is hydrogen. In some embodiments, R$^5$ is methyl.

In some embodiments, R$^2$ is hydrogen.

In some embodiments, R$^3$ is hydrogen. In some embodiments, R$^3$ is hydroxy-C$_2$-C$_4$-alkyl. In some embodiments, R$^3$ is —CH$_2$CH$_2$CH$_2$OH.

In some embodiments, n is 0.

In some embodiments, n is 1. In some embodiments, R$^4$ is selected from methoxy and nitro.

In some embodiments, the compound is selected from:

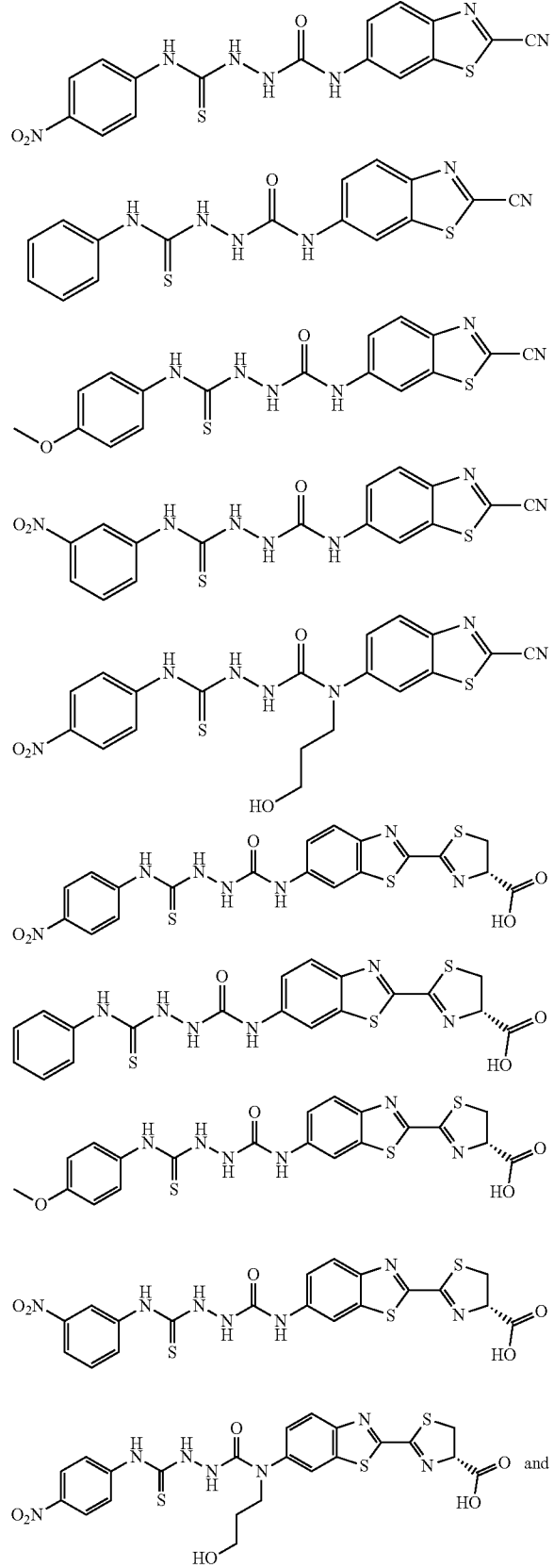
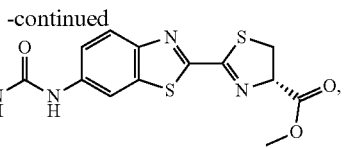

and salts thereof.

In some embodiments, the compound is in a salt form, i.e., a charged form of the parent compound associated with a counterion. A neutral form of the compound may be regenerated by contacting the salt with a base or acid and isolating the parent compound in a conventional manner. The parent form of the compound differs from the various salt forms in certain physical properties, such as solubility in polar solvents, but otherwise the salts are equivalent to the parent form of the compound for the purposes of this disclosure.

In particular, if a compound is anionic or has a functional group that may be anionic (e.g., —COOH may be —COO—), then a salt may be formed with one or more suitable cations. Examples of suitable inorganic cations include, but are not limited to, alkali metal cations such as Li$^+$, Na$^+$, and K$^+$, alkaline earth cations such as Ca$^{2+}$ and Mg$^{2+}$, and other cations. Potassium and sodium salts may be particularly suitable. Examples of suitable organic cations include, but are not limited to, ammonium ion (i.e., NH$_4^+$) and substituted ammonium ions (e.g., NH$_3$R$_1^+$, NH$_2$R$_2^+$, NHR$_3^+$, and NR$_4^+$). Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids such as lysine and arginine. In some embodiments, the compound is a potassium salt. In some embodiments, the compound is a sodium salt.

If a compound cationic or has a functional group that may be cationic (e.g., —NH$_2$ may be —NH$_3^+$), then a salt may be formed with a suitable anion. Examples of suitable inorganic anions include, but are not limited to, those derived from the following inorganic acids: hydrochloric, hydrobromic, hydroiodic, sulfuric, sulfurous, nitric, nitrous, phosphoric, and phosphorous. Examples of suitable organic anions include, but are not limited to, those derived from the following organic acids: 2-acetyoxybenzoic, acetic, ascorbic, aspartic, benzoic, camphorsulfonic, cinnamic, citric, edetic, ethanedisulfonic, ethanesulfonic, fumaric, glucoheptonic, gluconic, glutamic, glycolic, hydroxymaleic, hydroxynaphthalene carboxylic, isethionic, lactic, lactobionic, lauric, maleic, malic, methanesulfonic, mucic, oleic, oxalic, palmitic, pamoic, pantothenic, phenylacetic, phenylsulfonic, propionic, pyruvic, salicylic, stearic, succinic, sulfanilic, tartaric, tetrafluoroboric, toluenesulfonic, trifluoromethanesulfonic, and valeric. In some embodiments, the compound is a halide salt, such as a chloride, bromide, or iodide salt. In some embodiments, the compound is a tetrafluoroborate or trifluoromethanesulfonate salt.

The compounds can be prepared by a number of suitable methods, some of which are shown in the Examples. Compounds and intermediates may be isolated and purified by methods well-known to those skilled in the art of organic synthesis. Examples of conventional methods for isolating and purifying compounds can include, but are not limited to, chromatography on solid supports such as silica gel, alumina, or silica derivatized with alkylsilane groups, by recrystallization at high or low temperature with an optional pretreatment with activated carbon, thin-layer chromatography, distillation at various pressures, sublimation under vacuum, and trituration, as described for instance in "Vogel's Textbook of Practical Organic Chemistry," 5th edition (1989), by Furniss, Hannaford, Smith, and Tatchell, pub. Longman Scientific & Technical, Essex CM20 2JE, England.

Reaction conditions and reaction times for each individual step can vary depending on the particular reactants employed and substituents present in the reactants used. Reactions can be worked up in a conventional manner, e.g., by eliminating the solvent from the residue and further purified according to methodologies generally known in the art such as, but not limited to, crystallization, distillation, extraction, trituration, and chromatography. Unless otherwise described, the starting materials and reagents are either commercially available or can be prepared by one skilled in the art from commercially available materials using methods described in the chemical literature.

Standard experimentation, including appropriate manipulation of the reaction conditions, reagents and sequence of the synthetic route, protection of any chemical functionality that cannot be compatible with the reaction conditions, and deprotection at a suitable point in the reaction sequence of the method are included in the scope of the disclosure. Suitable protecting groups and the methods for protecting and deprotecting different substituents using such suitable protecting groups are well known to those skilled in the art; examples of which can be found in PGM Wuts and TW Greene, in Greene's book titled Protective Groups in Organic Synthesis (4$^{th}$ ed.), John Wiley & Sons, NY (2006).

When an optically active form of a disclosed compound is required, it can be obtained by carrying out one of the procedures described herein using an optically active starting material (prepared, for example, by asymmetric induction of a suitable reaction step), or by resolution of a mixture of the stereoisomers of the compound or intermediates using a standard procedure (such as chromatographic separation, recrystallization, or enzymatic resolution).

Similarly, when a pure geometric isomer of a compound is required, it can be obtained by carrying out one of the procedures described herein using a pure geometric isomer as a starting material, or by resolution of a mixture of the geometric isomers of the compound or intermediates using a standard procedure such as chromatographic separation.

The synthetic schemes and specific examples as described are illustrative and are not to be read as limiting the scope of the disclosure or the claims. Alternatives, modifications, and equivalents of the synthetic methods and specific examples are contemplated.

The present disclosure also includes isotopically-labeled compounds, which are identical to those recited in formula (I), but for the fact that one or more atoms are replaced by an atom having an atomic mass or mass number different from the atomic mass or mass number usually found in nature. Examples of isotopes suitable for inclusion in the compounds of the invention are hydrogen, carbon, nitrogen, oxygen, phosphorus, sulfur, fluorine, and chlorine, such as, but not limited to, $^2$H, $^3$H, $^{13}$C, $^{14}$C, $^{15}$N, $^{18}$O, $^{17}$O, $^{31}$P, $^{32}$P, $^{35}$S, $^{18}$F, and $^{36}$Cl, respectively. Isotopically-labeled compounds of formula (I) can generally be prepared by conventional techniques known to those skilled in the art or by processes analogous to those described in the accompanying Examples using appropriate isotopically-labeled reagent in place of non-isotopically-labeled reagent.

Methods of Use, Systems, and Kits

Disclosed herein are methods of detecting nitric oxide using the compounds disclosed herein (e.g., compounds of formula (I)). The compounds feature a reactive moiety, in particular:

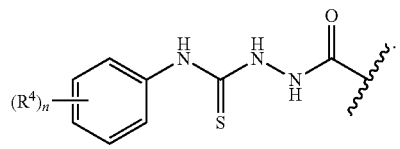

Without wishing to be bound by theory, the compounds are believed to react with nitric oxide as shown in Scheme 1. The product of NO and oxygen (dinitrogen trioxide) rapidly reacts with the sulfur of the reactive moiety, forming an intermediate diamino oxadiazole with concomitant release of a good leaving group, thio-nitrite. The oxadiazole readily hydrolyzes to release aminoluciferin or aminocyanobenzothiazole, which are substrates for a luciferin-utilizing luciferase enzyme, which produces luminescence. Luciferases that utilize luciferin, aminoluciferin, hydroxycyanobenzothiazole, and aminocyanobenzothiazole compounds to produce luminescence ("luciferin-utilizing luciferase" or "luciferin-utilizing luciferase enzyme") include those found in various organisms such as beetles (e.g., *Photinus pyralis* and *Photuris pennsylvanica* (fireflies of North America), *Pyrophorus plagiophthalamus* (the Jamaican click beetle)), *Renilla reniformis* (the sea pansy), and several bacteria (e.g., *Xenorhabdus luminescens* and *Vibrio* spp).

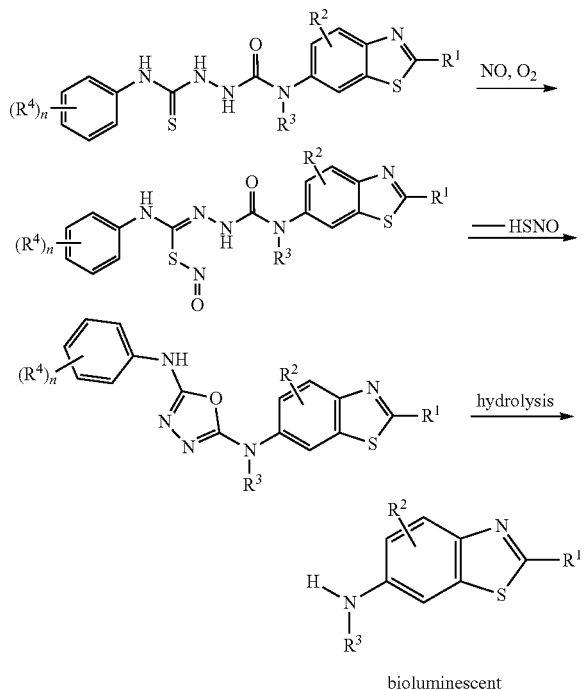

Prior to uncaging by reaction with nitric oxide, compounds of formula (I) are unreactive with the luciferase enzyme, such that luminescence is only observed in the presence of nitric oxide. The reactive moiety has been shown to be selective for nitric oxide over other reactive nitrogen and oxygen species (see, e.g., data in the Examples). Unlike more commonly used o-phenylene diamine based reactive moieties, which tend to react with bis electrophiles such as dehydroascorbic acid to generate false positives, false positives are less likely with the thiosemicarbazide moiety due to the two steps that must occur to release the reporter molecule (cyclization to oxadiazole followed by hydrolysis).

Another advantage of compounds of formula (I) is that the uncaged products are detected by bioluminescence, and no external light is needed (as with fluorescent probes). Furthermore, although nitric oxide species are unstable, upon reaction of the compounds of formula (I), with nitric oxide, the uncaged compounds are stable. As NO continues to be produced by the cells, the stable uncaged compounds will continue to accumulate and can be detected by measuring the light production (e.g., using the luciferase reaction). Light production will directly correlate with the production of NO and will offer a convenient and quantitative approach for detection of the short-lived NO. The uncaged aminoluciferin or aminocyanobenzothiazole compounds can be measured by adding the detection reagent directly to the sample using a homogenous "add and read" format or by measuring release of the luciferin derivatives into the media at different time points by media sampling and luciferin detection.

Accordingly, the present disclosure provides a method for detecting nitric oxide in a sample, the method comprising: contacting the sample with a compound of formula (I); contacting the sample with a luciferin-utilizing luciferase, if it is not already present in the sample; and detecting luminescence in the sample.

The methods comprise a step of contacting the sample with a compound of formula (I). The compound of formula (I) can be part of a solution that can include other components, such as a solvent, a buffer, a salt, a detergent, an additive, or the like. For example, the compound of formula (I) can be prepared as a solution in a solvent such as dimethylsulfoxide, or as a solution in a buffer such as phosphate-buffered saline. In some embodiments, the method comprises first contacting the sample with a compound of formula (I) and incubating the sample for a period of time, to allow nitric oxide to react with the compound of formula (I). In some embodiments, this incubation step can be conducted for a period of time of about 1 minute to about 4 days, about 15 minutes to about 1 day, about 1 hour to about 12 hours, or any range therebetween. For example, in some embodiments, the incubation step can be conducted for about 1 hour, about 2 hours, about 3 hours, about 4 hours, about 5 hours, about 6 hours, about 7 hours, about 8 hours, about 9 hours, about 10 hours, about 11 hours, or about 12 hours.

In particular embodiments, a luciferin-utilizing luciferase is not already present in the sample, and accordingly the method comprises a step of contacting the sample with the luciferin-utilizing luciferase. In some embodiments, the luciferin-utilizing luciferase is a firefly luciferase or a click beetle luciferase.

When the luciferin-utilizing luciferase is contacted with the sample, it may be included as part of a luciferase reaction mixture. A "luciferase reaction mixture" contains a luciferin-utilizing luciferase enzyme and other materials that will allow the luciferase enzyme to generate a light signal. The materials needed, and the particular concentrations and/or amounts, of the materials needed to generate a luminescent signal will vary depending on the luciferase enzyme being used. In general, for beetle luciferases, the additional materials can include ATP and a magnesium ($Mg^{2+}$) salt such as magnesium sulfate. In some embodiments, other materials can be added to the solution including: a buffer to maintain the reaction at the proper pH, an additive such as PRIONEX or Bovine serum albumin (BSA) to help maintain luciferase activity, reducing agents, detergents, esterases, salts, amino acids (e.g., D-cysteine), etc. An exemplary luciferase reaction mixture would contain a beetle luciferase, $MgSO_4$, ATP, Tergitol NP-9, and Tricine.

In other embodiments, a luciferin-utilizing luciferase is already present in the sample. For example, in such embodiments, the sample may comprise cells that express a luciferin-utilizing luciferase enzyme.

In some embodiments of the above methods, the method further comprises a step of contacting the sample with another compound, such as a candidate drug compound or any compound for which it would be useful to determine the amount of nitric oxide produced when the compound is contacted with a sample. In such embodiments, the compound can be contacted with the sample at the same time as the compound of formula (I), or can be added to the sample after the compound of formula (I) has been added.

In an embodiment of a cell-based assay, the cells may be lysed in an appropriate lysis buffer. For animal cells, a buffer with 0.1-1.0% non-ionic detergents such as Triton X 100 or Tergitol is typically sufficient. Bacteria, plant, fungal or yeast cells are usually more difficult to lyse. Detergents, freeze/thaw cycles, hypotonic buffers, sonication, cavitation, or combinations of these methods may be used. The method of lysis that produces a lysate is compatible with luciferase or other enzyme activity, or the detection of other molecules or conditions.

In any of the above embodiments, the sample may be contained within any suitable vessel. For example, the sample may be in a vial or in a well of a plate (e.g., a 96-well plate).

In some embodiments, rather than detecting luminescence directly in a well of a plate (e.g., a 96-well plate) using a plate reader, luciferin released into the media can be monitored by removing small amounts of media from the sample and detecting luminescence in the removed media. Such a method can allow for kinetic information on nitric oxide generation.

The present disclosure further provides a system or kit comprising a compound described herein (i.e., a compound of formula (I) or a salt thereof). The system or kit includes the compound, either alone or in a solvent such as water, DMSO, or a buffer. When the compound is provided alone, the system or kit may further include the solvent in which the compound can be dissolved. The system or kit may further comprise one or more reagents used to carry out an assay to detect nitric oxide in a sample, e.g., a reagent described above. The system or kit may further comprise instructions, such as instructions for carrying out an assay to detect nitric oxide in a sample.

The following examples further illustrate aspects of the disclosure but, of course, should not be construed as in any way limiting its scope.

EXAMPLES

The following abbreviations are used in the Examples: AcOH is acetic acid; DCE is dichloroethane; DIPEA is N,N-diisopropylethylamine; DMF is N,N-dimethylformamide; DMSO is dimethylsulfoxide; ES is electrospray; EtOAc is ethyl acetate; h is hours; HPLC is high performance liquid chromatography; LCMS is liquid chromatography mass spectrometry; MeCN is acetonitrile; TFA is trifluoroacetic acid; and THF is tetrahydrofuran.

Example 1: Compound Syntheses

Intermediate 1: 6-((3-((tert-butyldimethylsilyl)oxy)propyl)amino)benzo[d]thiazole-2-carbonitrile

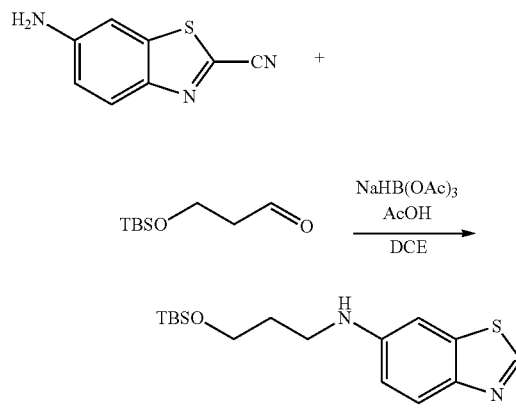

To a 20 mL vial, 6-aminobenzo[d]thiazole-2-carbonitrile (100 mg, 0.571 mmol), 3-((tert-butyldimethylsilyl)oxy)propanal (118 mg, 0.628 mmol), DCE (1.5 mL), and AcOH (0.034 mL, 0.57 mmol) was added. The mixture was stirred at 60° C. for 15 min. The mixture was cooled to RT. To the mixture, sodium triacetoxyborohydride (181 mg, 0.856 mmol) was added. After 1 h, the mixture was purified silica gel chromatography with 0-50% EtOAc in heptane as eluent to afford Intermediate 1 6-((3-((tert-butyldimethylsilyl)oxy)propyl)amino)benzo[d]thiazole-2-carbonitrile. LCMS ($C_{17}H_{25}N_3OSSi$) (ES, m/z) 348 [M+H]$^+$.

Compound 1: N-(2-cyanobenzo[d]thiazol-6-yl)-2-((4-nitrophenyl)carbamothioyl)hydrazine-1-carboxamide

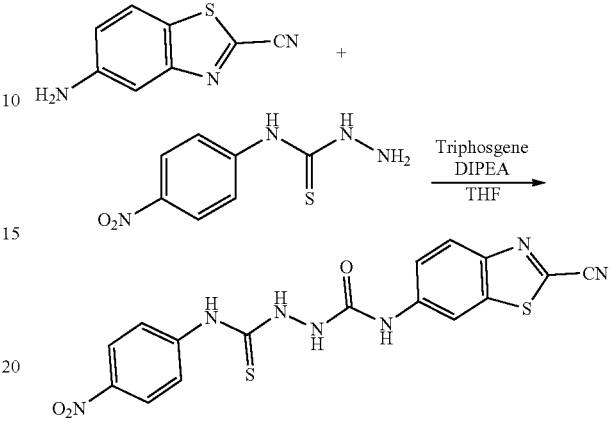

To a 20 mL vial, triphosgene (84.7 mg, 0.285 mmol) and THF (3 mL) was added. The mixture was stirred. To the mixture, a solution of 6-aminobenzo[d]thiazole-2-carbonitrile (100 mg, 0.571 mmol) and DIPEA (0.399 mL, 2.28 mmol) in THF (3 mL) was added dropwise. After 5 min, to the mixture, N-(4-nitrophenyl)hydrazinecarbothioamide (242 mg, 1.14 mmol) was added. After 30 min, the mixture was concentrated and purified by reversed phase HPLC (MeCN/water w/0.1% TFA) to afford Compound 1 N-(2-cyanobenzo[d]thiazol-6-yl)-2-((4-nitrophenyl)carbamothioyl)hydrazine-1-carboxamide. LCMS ($C_{16}H_{11}N_7O_3S_2$) (ES, m/z) 414 [M+H]$^+$. $^1$H NMR (400 MHz, DMSO-d$_6$) δ 10.27 (s, 1H), 9.99 (s, 1H), 9.55 (s, 1H), 8.59 (d, J=13.8 Hz, 2H), 8.20 (dd, J=19.2, 8.5 Hz, 3H), 7.98 (d, J=8.7 Hz, 2H), 7.77 (d, J=9.1 Hz, 1H).

The compounds in the following Table 1 were prepared in an analogous manner to that of Compound 1.

TABLE 1

| Compound | Name | Structure | (ES, m/z) [M + H]$^+$ |
|---|---|---|---|
| 2 | N-(2-cyanobenzo[d]thiazol-6-yl)-2-(phenylcarbamothioyl)hydrazine-1-carboxamide | 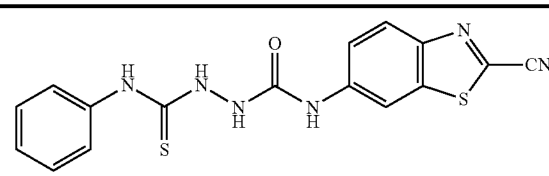 | 369 |
| 3 | N-(2-cyanobenzo[d]thiazol-6-yl)-2-((4-methoxyphenyl)carbamothioyl)hydrazine-1-carboxamide | 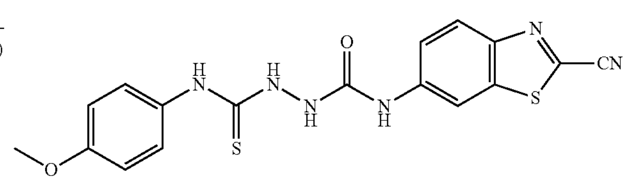 | 399 |
| 4 | N-(2-cyanobenzo[d]thiazol-6-yl)-2-((3-nitrophenyl)carbamothioyl)hydrazine-1-carboxamide | 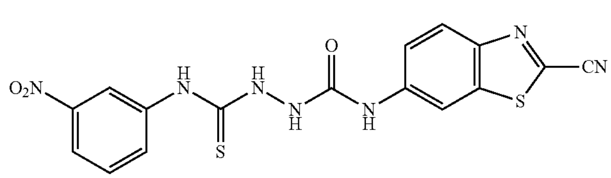 | 414 |

Compound 5: N-(2-cyanobenzo[d]thiazol-6-yl)-N-(3-hydroxypropyl)-2-((4-nitrophenyl)carbamothioyl)hydrazine-1-carboxamide

Step 1: N-(3-((tert-butyldimethylsilyl)oxy)propyl)-N-(2-cyanobenzo[d]thiazol-6-yl)-2-((4-nitrophenyl)carbamothioyl)hydrazine-1-carboxamide

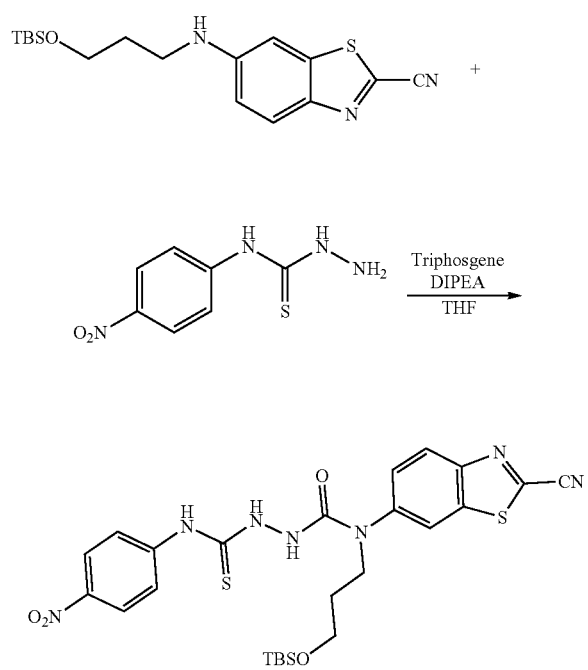

N-(3-((tert-butyldimethylsilyl)oxy)propyl)-N-(2-cyanobenzo[d]thiazol-6-yl)-2-((4-nitrophenyl)carbamothioyl)hydrazine-1-carboxamide was prepared from Intermediate 1 in an analogous manner to Compound 1. LCMS ($C_{25}H_{31}N_7O_4S_2Si$) (ES, m/z) 586 [M+H]$^+$.

Step 2: N-(2-cyanobenzo[d]thiazol-6-yl)-N-(3-hydroxypropyl)-2-((4-nitrophenyl)carbamothioyl)hydrazine-1-carboxamide

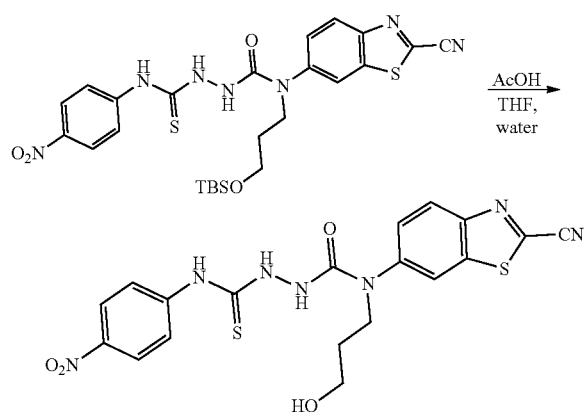

To a 20 mL vial, N-(3-((tert-butyldimethylsilyl)oxy)propyl)-N-(2-cyanobenzo[d]thiazol-6-yl)-2-((4-nitrophenyl)carbamothioyl)hydrazine-1-carboxamide (22.7 mg, 0.0388 mmol), THF (1 mL), AcOH (1 mL), and water (0.5 mL) was added. The mixture was stirred at room temperature. After 5 hours, the solvents were evaporated. The residue was purified by reversed phase HPLC (MeCN/water w/0.1% TFA) to afford Compound 5 N-(2-cyanobenzo[d]thiazol-6-yl)-N-(3-hydroxypropyl)-2-((4-nitrophenyl)carbamothioyl)hydrazine-1-carboxamide. LCMS ($C_{19}H_{17}N_7O_4S_2$) (ES, m/z) 472 [M+H]$^+$. $^1$H NMR (400 MHz, DMSO-d$_6$) δ 10.13 (d, J=245.7 Hz, 1H), 8.58 (d, J=25.8 Hz, 1H), 8.45-8.27 (m, 2H), 8.22 (d, J=8.7 Hz, 2H), 7.95 (d, J=8.4 Hz, 2H), 7.80 (d, J=9.3 Hz, 1H), 4.44 (s, 1H), 3.83 (d, J=8.3 Hz, 3H), 3.11 (s, 1H), 1.67 (s, 2H). NMR spectrum indicates presence of rotamers.

Compound 6: (S)-2-(6-(2-((4-nitrophenyl)carbamothioyl)hydrazine-1-carboxamido)benzo[d]thiazol-2-yl)-4,5-dihydrothiazole-4-carboxylic acid

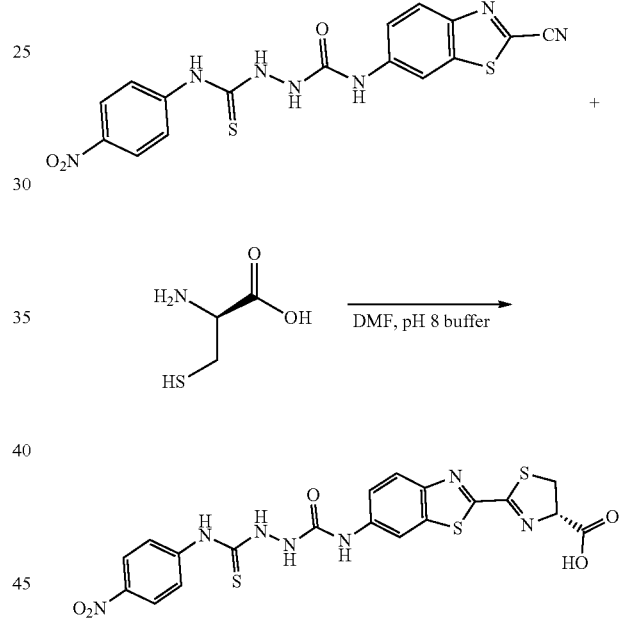

To a 20 mL vial containing Compound 1 N-(2-cyanobenzo[d]thiazol-6-yl)-2-((4-nitrophenyl)carbamothioyl)hydrazine-1-carboxamide (20.0 mg, 0.0484 mmol), DMF (5 mL) was added. The mixture was stirred. To the mixture, a solution of D-cysteine (7.0 mg, 0.058 mmol) in pH 8 phosphate buffer (1.5 mL) was added. The mixture was purified by reversed phase HPLC (MeCN/water w/0.1% TFA) to afford Compound 6 (S)-2-(6-(2-((4-nitrophenyl)carbamothioyl)hydrazine-1-carboxamido)benzo[d]thiazol-2-yl)-4,5-dihydrothiazole-4-carboxylic acid. LCMS ($C_{19}H_{15}N_7O_5S_3$) (ES, m/z) 518 [M+H]$^+$. $^1$H NMR (400 MHz, DMSO-d$_6$) δ 10.26 (s, 1H), 9.98 (s, 1H), 9.41 (s, 1H), 8.56 (s, 1H), 8.45 (s, 1H), 8.22 (d, J=8.7 Hz, 2H), 8.07 (d, J=8.9 Hz, 1H), 7.99 (d, J=8.7 Hz, 2H), 7.64 (d, J=9.0 Hz, 1H), 5.43 (t, J=9.1 Hz, 1H), 3.79 (t, J=10.6 Hz, 1H), 3.69 (dd, J=11.2, 8.4 Hz, 1H).

The compounds in the following Table 2 were prepared in an analogous manner to that of Compound 6.

TABLE 2

| Compound | Name | Structure | (ES, m/z) [M + H]+ |
|---|---|---|---|
| 7 | (S)-2-(6-(2-(phenylcarbamothioyl)hydrazine-1-carboxamido)benzo[d]thiazol-2-yl)-4,5-dihydrothiazole-4-carboxylic acid | 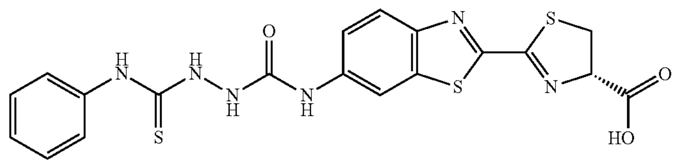 | 473 |
| 8 | (S)-2-(6-(2-((4-methoxyphenyl)carbamothioyl)hydrazine-1-carboxamido)benzo[d]thiazol-2-yl)-4,5-dihydrothiazole-4-carboxylic acid | 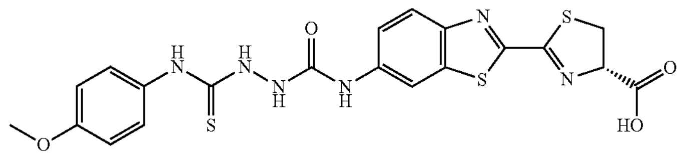 | 503 |
| 9 | (S)-2-(6-(2-((3-nitrophenyl)carbamothioyl)hydrazine-1-carboxamido)benzo[d]thiazol-2-yl)-4,5-dihydrothiazole-4-carboxylic acid | 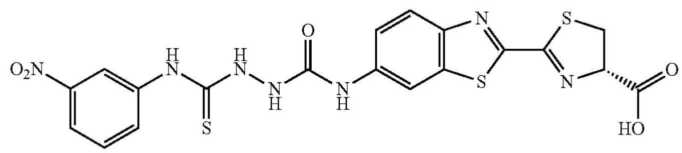 | 518 |
| 10 | (S)-2-(6-(N-(3-hydroxypropyl)-2-((4-nitrophenyl)carbamothioyl)hydrazine-1-carboxamido)benzo[d]thiazol-2-yl)-4,5-dihydrothiazole-4-carboxylic acid | 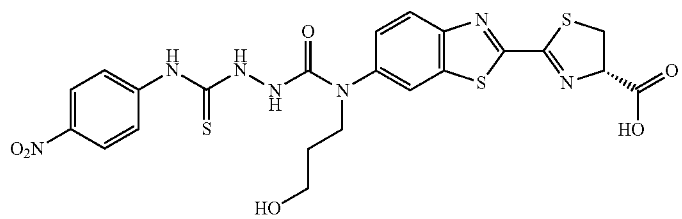 [SMILES: O=C(O)[C@H]1CSC(c2nc3ccc(N(CCCO)C(=O)NNC(=S)Nc4ccc([N+](=O)[O-])cc4)cc3s2)=N1] | 576 |

Compound 11: Methyl (S)-2-(6-(2-((4-nitrophenyl)carbamothioyl)hydrazine-1-carboxamido)benzo[d]thiazol-2-yl)-4,5-dihydrothiazole-4-carboxylate

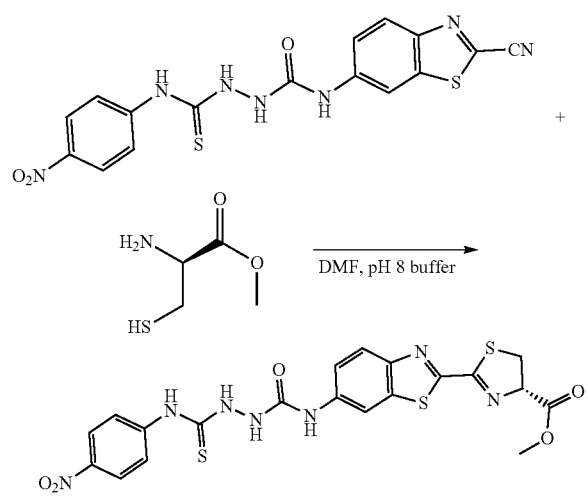

To a 20 mL vial containing Compound 1 N-(2-cyanobenzo[d]thiazol-6-yl)-2-((4-nitrophenyl)carbamothioyl)hydrazine-1-carboxamide (7.7 mg, 0.0186 mmol), DMF (2 mL) was added. The mixture was stirred. To the mixture, a solution of D-cysteine methyl ester (3.0 mg, 0.022 mmol) in pH 8 phosphate buffer (1 mL) was added. The mixture was purified by reversed phase HPLC (MeCN/water w/0.1% TFA) to afford Compound 11 (methyl (S)-2-(6-(2-((4-nitrophenyl)carbamothioyl)hydrazine-1-carboxamido)benzo[d]thiazol-2-yl)-4,5-dihydrothiazole-4-carboxylate). LCMS ($C_{20}H_{17}N_7O_5S_3$) (ES, m/z) 532 [M+H]+. $^1$H NMR (400 MHz, DMSO-$d_6$) δ 10.26 (s, 1H), 10.11-9.86 (m, 1H), 9.42 (s, 1H), 8.56 (s, 1H), 8.45 (s, 1H), 8.22 (dd, J=9.1, 2.6 Hz, 2H), 8.12-8.04 (m, 1H), 7.99 (d, J=8.1 Hz, 2H), 7.63 (d, J=9.1 Hz, 1H), 6.51 (d, J=16.7 Hz, 1H), 5.54 (t, J=9.2 Hz, 1H), 3.82 (t, J=10.7 Hz, 1H), 3.77 (s, 3H), 3.71 (t, J=9.6 Hz, 1H).

Example 2: Cell-Free Nitric Oxide Detection

Figure 3:
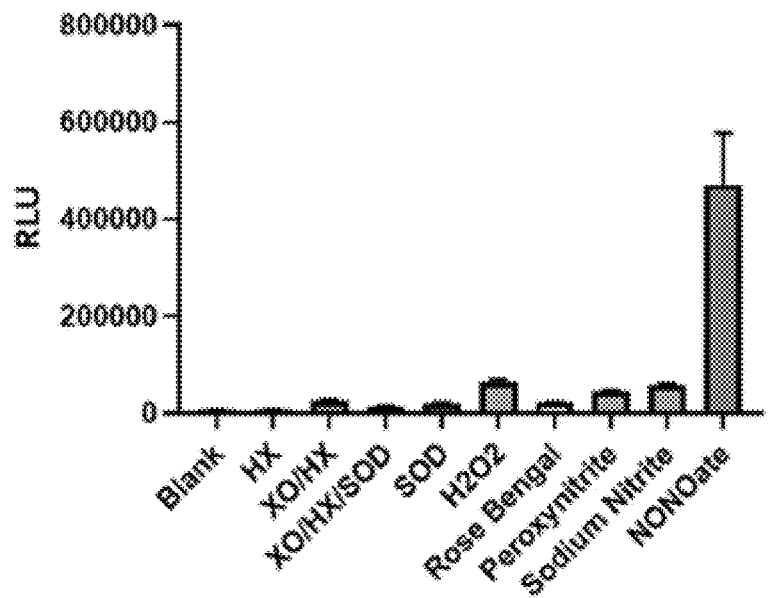
FIG. 3 shows data from assays to detect nitric oxide in cell-free samples, as described in Example 2.

Cell-free detection and specificity of nitric oxide (NO) using reactive oxygen species (hypoxanthine (HX; 25 μM), xanthine oxidase (XO; 0.2 units/mL), superoxide dismutase (SOD 1 unit/mL), hydrogen peroxide ($H_2O_2$ 0.03%), oxygen singlet (Rose Bengal; 25 μM), and reactive nitrogen species (sodium nitrite; 100 μM and peroxynitrite; 50 μM) was compared with a known NO donor, NONOate (100 μM). A NO probe (Compound 6, 25 μM) was combined with the analytes described above in wells of a 96-well assay plate with PBS. Each well of the 96-well assay plate contained 50 μL of a nitric oxide probe and 50 μL of an analyte. Following a 30-minute incubation at room temperature, 100 μL of luciferin detection reagent (Promega) was added, and luminescence measured using a GloMax (Promega) luminometer. Data are presented in FIG. 3 (RLU=relative light units).

Example 3: Detection of Nitric Oxide in Cells Following Synergistic NO Stimulation with Lipopolysaccharide (LPS) and Interferon Gamma (INFy)

Figure 4:
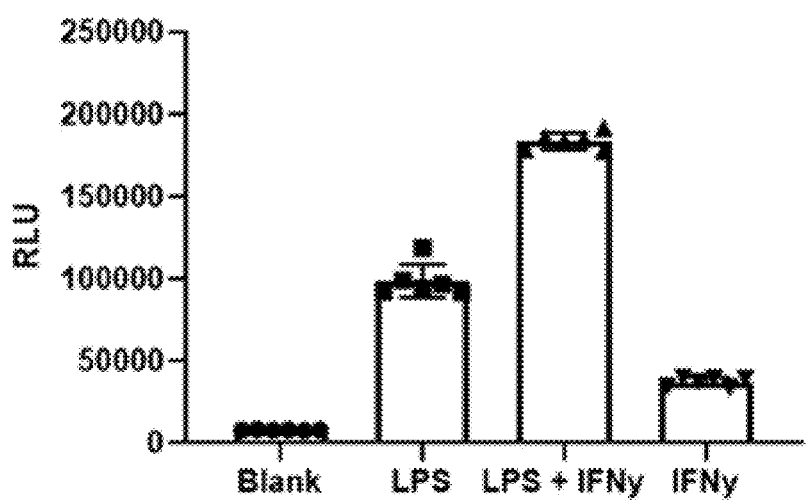
FIG. 4 shows data from assays to detect nitric oxide in cells following synergistic NO stimulation with lipopolysaccharide (LPS) and interferon gamma (INFT), as described in Example 3.

TIB71 macrophage cells (30,000 cells per well) were seeded into wells of a 96-well assay plate with 100 μL DMEM medium containing 10% FBS. The following day, the medium was removed and replaced with fresh DMEM medium containing 10% FBS and a nitric oxide probe (Compound 6, 25 μM) coupled medium (blank), LPS (1 ug/mL), and/or INFy (1 ng/mL). Following a 24-hour incubation at 37° C. in a tissue culture incubator, one volume of luciferin detection reagent (Promega) was added, and luminescence measured using a GloMax (Promega) luminometer. Data are presented in FIG. 4 (RLU=relative light units).

Example 4: Detection of Nitric Oxide in SIN-1 Treated Cells

Figure 5A:
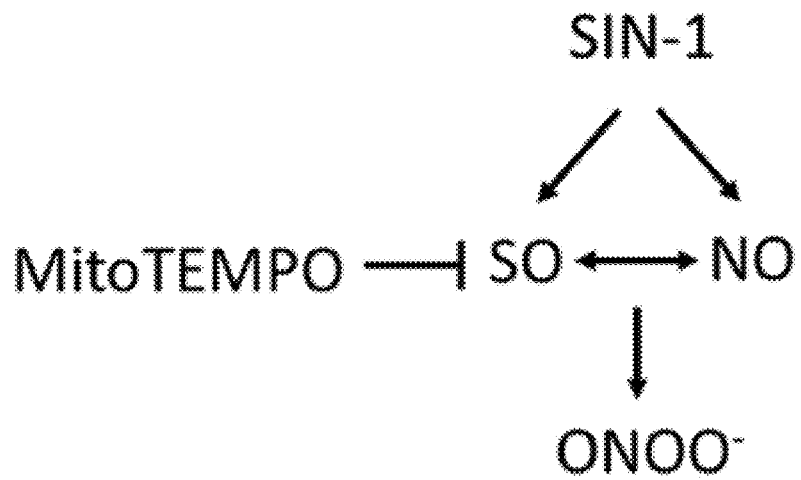
FIGS. 5A-5B show a schematic of SIN-1 induction of superoxide (SO) and NO, in which MitoTEMPO is used as a superoxide scavenger to increase NO levels (FIG. 5A), and data from assays to detect NO in five different cell lines treated with SIN-1 and MitoTEMPO, as described in Example 4.
Figure 5B:
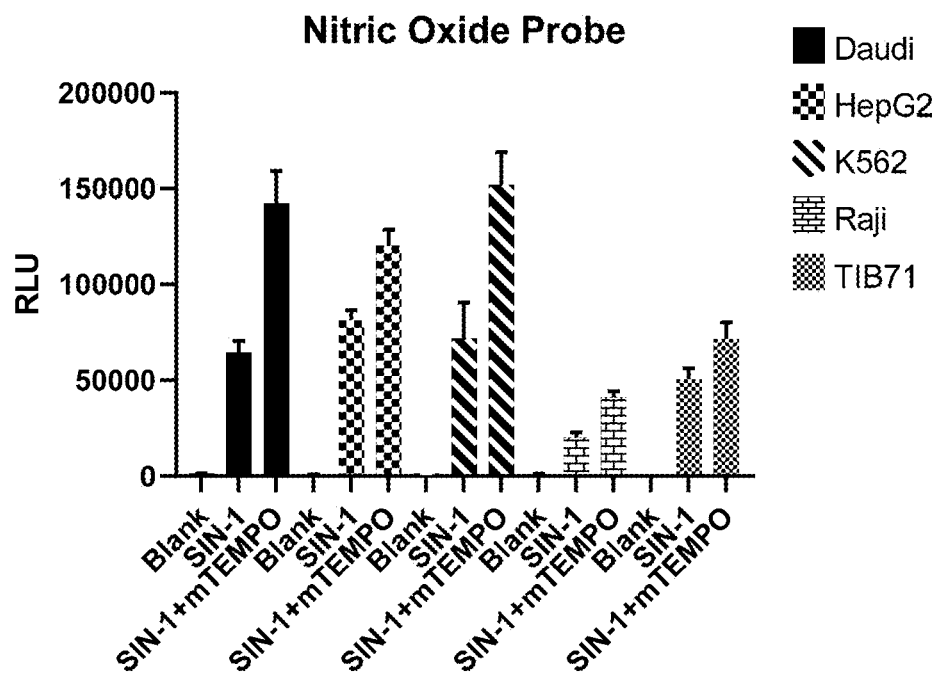

Under physiological conditions, SIN-1 generates superoxide (SO) and nitric oxide (NO) (see FIG. 5A). NO reacts readily reacts with SO to form peroxynitrite. MitoTEMPO is a SO scavenger that reduces SO levels and subsequently increases NO. Five cell lines (30,000 cells per well) were seeded into wells of 96-well assay plates and incubated overnight in a 37° C. tissue culture incubator. The following day, the NO probe (Compound 6, 25 μM) was coupled with medium (blank), SIN-1 (100 μM), or SIN-1 (100 μM) and MitoTEMPO (200 μM). After a 2-hour incubation at 37 C, one volume of luciferin detection reagent (Promega) was added, and luminescence measured using a GloMax (Promega) luminometer. Data are presented in FIG. 5B (RLU=relative light units).

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A compound of formula (I):

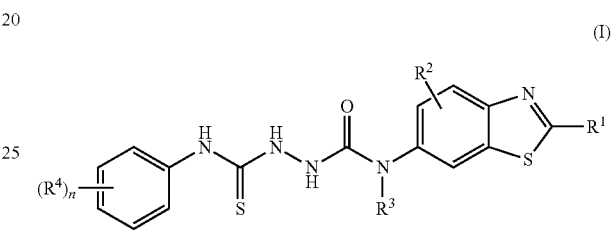

or a salt thereof, wherein:

$R^1$ is selected from —CN and

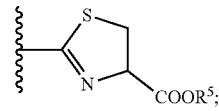

$R^2$ is selected from hydrogen and halo;
$R^3$ is selected from hydrogen, $C_1$-$C_6$ alkyl, and hydroxy-$C_1$-$C_6$-alkyl;
n is 0, 1, 2, or 3;
each $R^4$ is independently selected from $C_1$-$C_6$ alkyl, $C_2$-$C_6$ alkenyl, $C_2$-$C_6$ alkynyl, $C_1$-$C_6$ heteroalkyl, $C_1$-$C_6$ alkoxy, $C_1$-$C_6$ haloalkyl, $C_1$-$C_6$ haloalkoxy, halo, hydroxy, amino, cyano, nitro, —COO$R^a$, and —CONR$^b$R$^c$;
$R^5$ is selected from hydrogen and $C_1$-$C_4$ alkyl; and
$R^a$, $R^b$, and $R^c$ are each independently selected from hydrogen, $C_1$-$C_6$ alkyl, $C_2$-$C_6$ alkenyl, $C_2$-$C_6$ alkynyl, and $C_1$-$C_6$ heteroalkyl.

2. The compound of claim 1, or a salt thereof, wherein $R^1$ is —CN.

3. The compound of claim 1, or a salt thereof, wherein $R^1$ is

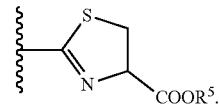

4. The compound of claim 3, or a salt thereof, wherein $R^5$ is selected from hydrogen and methyl.

5. The compound of claim 1, or a salt thereof, wherein $R^2$ is hydrogen.

6. The compound of claim 1, or a salt thereof, wherein $R^3$ is hydrogen.

7. The compound of claim 1, or a salt thereof, wherein $R^3$ is hydroxy-$C_2$-$C_4$-alkyl.

8. The compound of claim 7, or a salt thereof, wherein $R^3$ is —$CH_2CH_2CH_2OH$.

9. The compound of claim 1, or a salt thereof, wherein n is 0.

10. The compound of claim 1, or a salt thereof, wherein n is 1.

11. The compound of claim 10, or a salt thereof, wherein $R^4$ is selected from methoxy and nitro.

12. The compound of claim 1, selected from:

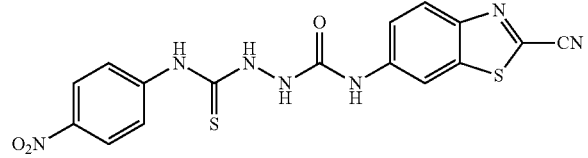

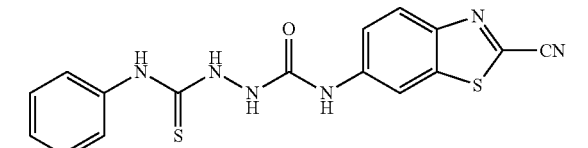

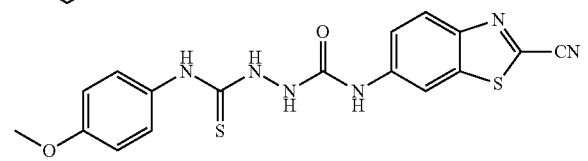

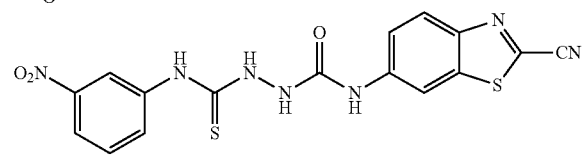

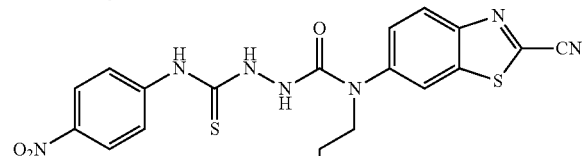

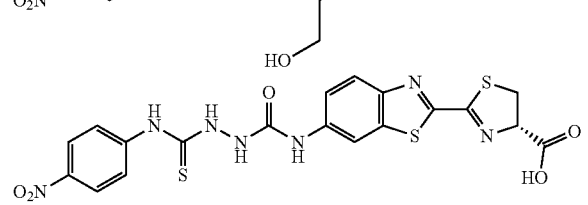

-continued

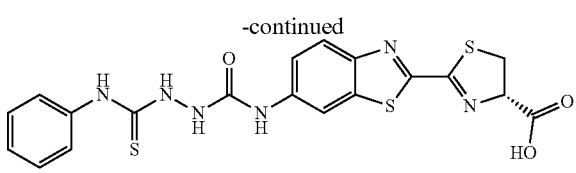

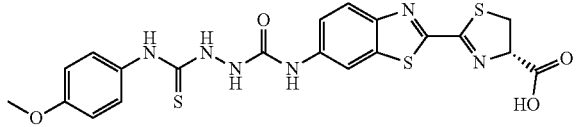

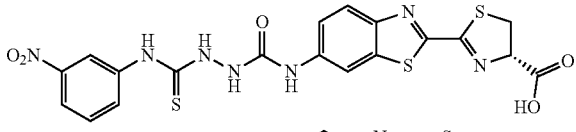

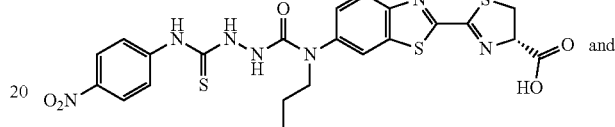 and

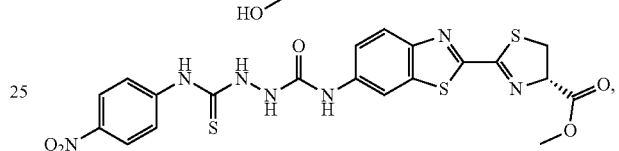

or a salt thereof.

13. A method of detecting nitric oxide in a sample, comprising:
   contacting the sample with a compound of claim 1, or a salt thereof,
   contacting the sample with a luciferin-utilizing luciferase, if it is not already present in the sample; and
   detecting luminescence in the sample.

14. The method of claim 13, wherein the sample comprises live cells.

15. The method of claim 14, wherein the cells express the luciferin-utilizing luciferase.

16. The method of claim 13, comprising adding the luciferin-utilizing luciferase to the sample.

17. The method of claim 1, wherein the luciferin-utilizing luciferase is a firefly luciferase or a click beetle luciferase.

18. A kit comprising a compound of claim 1, or a salt thereof.

19. The kit of claim 18, further comprising a luciferin-utilizing luciferase enzyme or a nucleotide sequence encoding a luciferin-utilizing luciferase enzyme.

20. The kit of claim 18, further comprising a buffer reagent.

* * * * *